Aug. 7, 1962 C. B. THOMAS Plant Pat. 2,161
WATER LILY PLANT
Filed Oct. 4, 1961 2 Sheets-Sheet 1
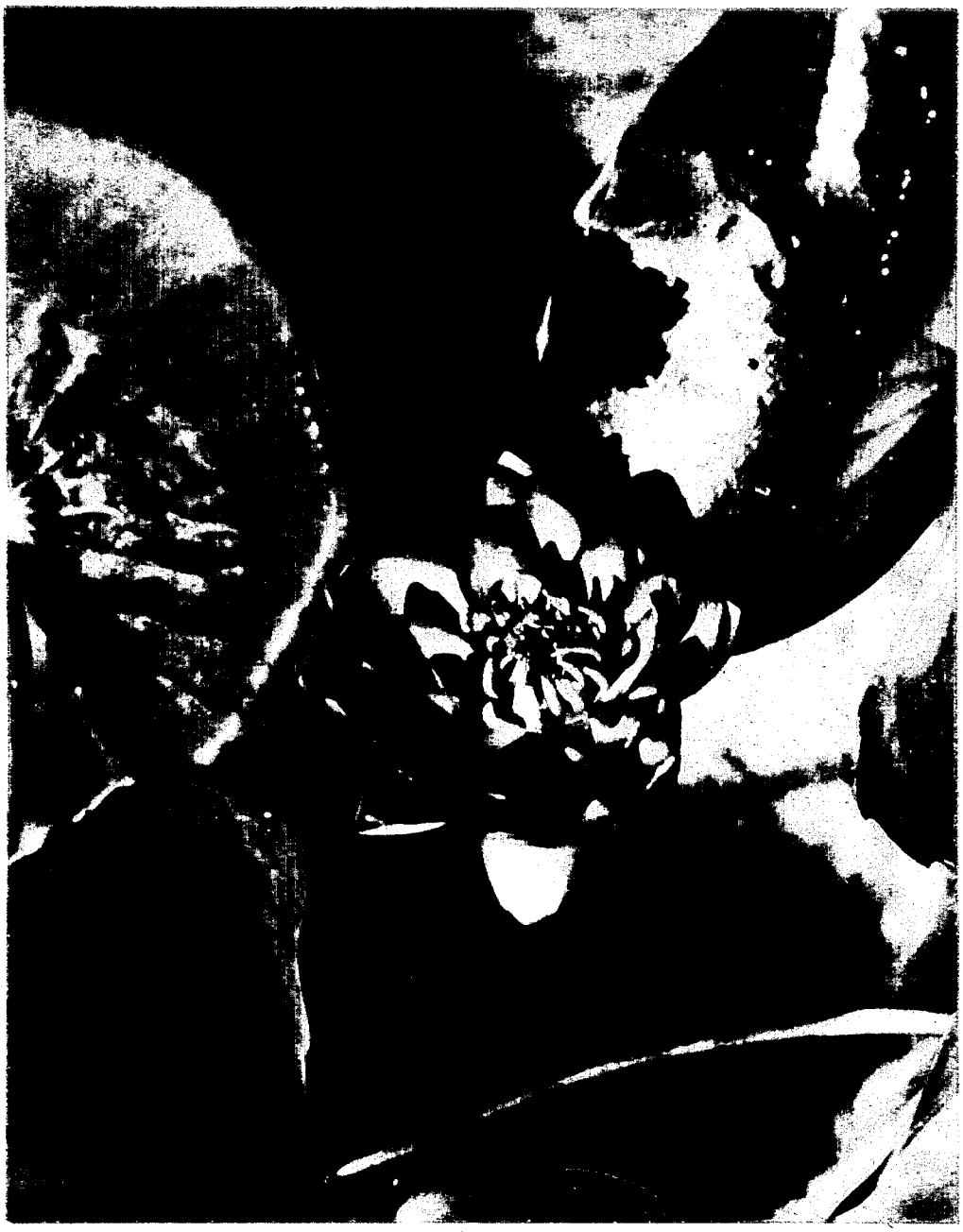
INVENTOR
Charles Brosius Thomas
BY Robb & Robb
ATTORNEYS WATER LILY PLANT
Filed Oct. 4, 1961 2 Sheets-Sheet 2
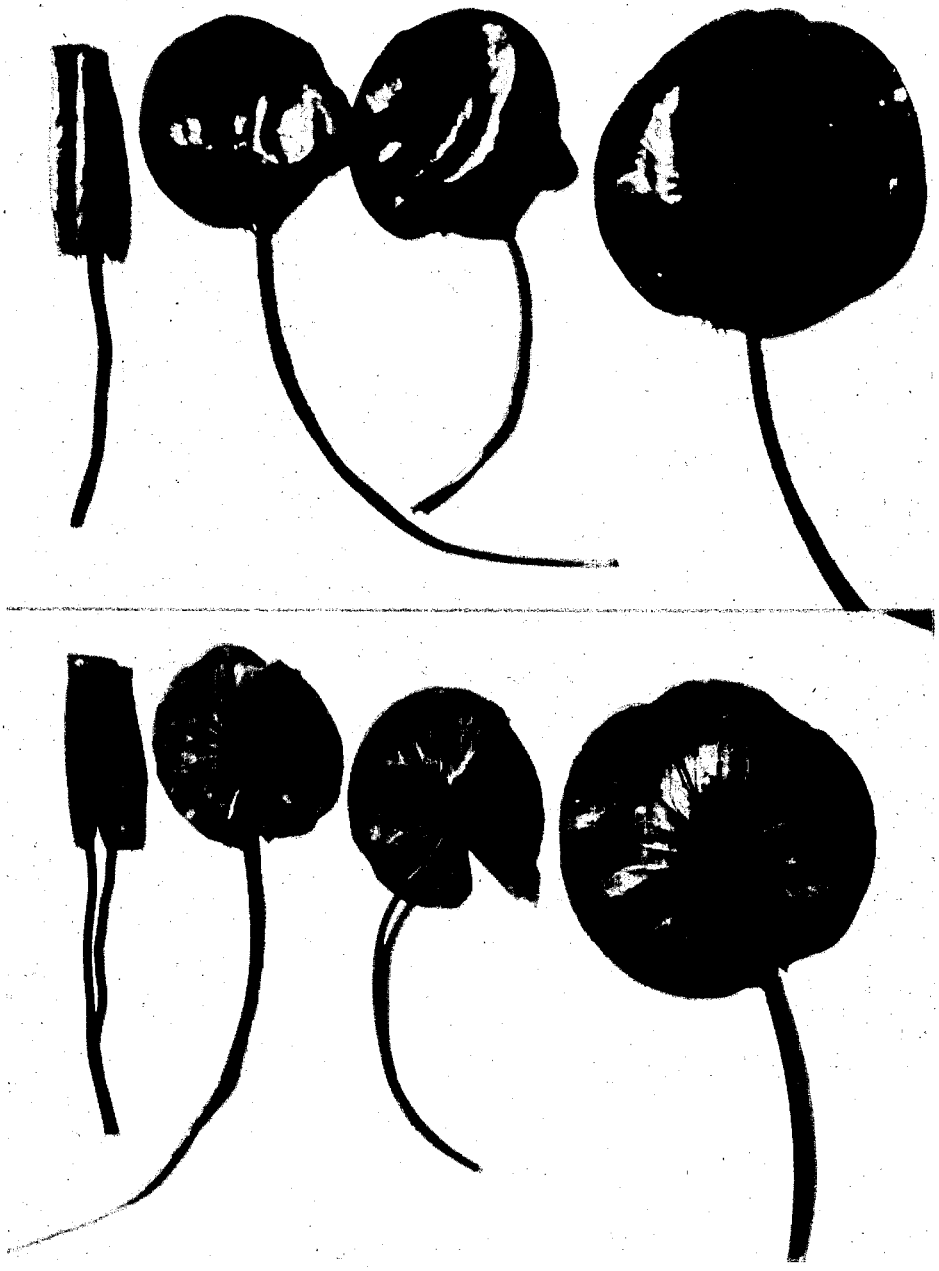
INVENTOR
Charles Brosius Thomas
BY Robb & Robb
ATTORNEYS United States Patent Office Plant Pat. 2,161
Patented Aug. 7, 1962

2,161
WATER LILY PLANT
Charles Brosius Thomas, Lilypons, Md.
Filed Oct. 4, 1961, Ser. No. 142,993
1 Claim. (Cl. 47—60)

The present invention relates to a new and distinct variety of water lily, which was originated by me by crossing the variety known as "Escarboucle" (unpatented) with the variety known as "Mrs. C. W. Thomas" (unpatented).

As the result of this breeding, I have produced a new variety of water lily which is unique and distinct from all other varieties of which I am aware, as evidenced by the following combination of outstanding characteristics which are found in the new variety and which distinguish it from its parents, as well as from all other varieties:

(1) Ease of growth;
(2) Good blooming habits;
(3) Double flower form; and
(4) An attractive and distinctive Dark Red general color tonality of the flowers, which are the deepest in color of all Red Water Lilies within my knowledge or heretofore available in commerce.

Asexual reproduction of my new water lily by rhizome division, as performed by me at Lilypons, Maryland, shows that the foregoing characteristics and distinctions are fixed and come true, and are transmissible through succeeding propagations.

The accompanying drawings show typical specimens of the flowers and foliage of my new variety in different stages of development and as depicted in color as nearly true as it is reasonably possible to make the same in a color illustration of this character, with both the upper and under surfaces of main leaf specimens and one curled submerged leaf specimen being shown.

The following is a detailed description of my new water lily, as based upon observations of specimens grown in ponds at Lilypons, Maryland, with color terminology in accordance with general color terms of ordinary dictionary significance, except where the colors correspond to those of Nickerson's Color Fan, published by Munsell Color Company of Baltimore, Maryland, as indicated:

Parentage: Seedling.
*Seed parent.*—"Escarboucle."
*Pollen parent.*—"Mrs. C. W. Thomas."
Propagation: Holds its distinguishing characteristics through succeeding propagations by rhizome division.

*Plant*

Foliage:
*Submerged leaves.*—Shape—round; curled. Length (from petiole to sinus)—2 inches. Color: Upper side — Reddish-Green. Under side — Reddish-Green.
*Main floating leaves.*—Shape—round. Length (from petiole to sinus)—3½ inches. Color—Dark Green.
*Mature leaves.*—Shape—round. Size—from 8 to 9 inches. Color: Upper side—Dark Green. Under side—green, with red cast extending from, margin to near mid-rib. Leaf stem: Color—near Strong Reddish Orange, Plate 7.5R5/13 (Nickerson). Length—about 20 inches, depending on growing conditions.

*Flower*

Bloom:
*Blooming habit.*—From late May through early September.
*Color.*—*Dark Red,* varying between near Moderate Red, Plate 2.5R4/10 (Nickerson) and near Strong Red, Plate 5R4/12 (Nickerson).
*Size.*—5 inches.
*Number of days open.*—4 days.
*Number open at one time.*—1 or 2.
*Distance standing out of water.*—Floats.
*Fragrance.*—Faint. Nature—sweet.
Buds:
*Shape.*—Normal; corresponds to the buds of cup-shaped water lily.
*Color.*—Dark Green.
Scape: Color—white.
Sepals:
*Number.*—4.
*Color.*—Brown-Green.
*Length.*—2¼ inches.
*Width.*—¾ inch.
*Shape.*—Elliptical.
*Texture.*—Smooth.
Petals:
*Number.*—32.
*Shape.*—Elliptical.
*Length.*—2¼ inches.
*Width.*—⅝ inch.
*Color.*—Dark Red.
Stamens:
*Number.*—70.
*Length.*—Outer—1½ inches. Inner—½ inch.
*Appendages.*—With.
Carpels:
*Number.*—16.
*Length.*—¼ inch.
*Color.*—Yellow.
Stigma: Color—yellow.
Lasting Quality: Very good.
Shipping Quality: Very good.

*Fruit*

Shape: Basically cylindrical, but with top having slightly larger diameter.
Size:
*Height.*—½ inch.
*Width.*—¾ inch.
Seeds: Present; fertile.

I claim:

A new and distinct variety of water lily plant, substantially as herein shown and described, characterized particularly as to novelty by the unique combination of ease of growth, good blooming habits, double flower form, and an attractive and distinct Dark Red general color tonality of the flowers.

No references cited.